United States Patent [19]

Green

[11] Patent Number: 4,672,144
[45] Date of Patent: Jun. 9, 1987

[54] FLAME CONVERSION OF METHANE TO MORE REACTIVE HYDROCARBONS

[75] Inventor: Gary J. Green, Yardley, Pa.

[73] Assignee: Mobil Oil Corporation, New York, N.Y.

[21] Appl. No.: 796,366

[22] Filed: Nov. 8, 1985

[51] Int. Cl.$^4$ .............................................. C07C 2/78
[52] U.S. Cl. ................... 585/540; 208/106; 585/403; 585/503; 585/505; 585/537; 585/539; 585/615; 585/636; 585/652; 585/943
[58] Field of Search ............... 585/403, 503, 505, 537, 585/539, 540, 615, 636, 652, 943; 208/106, 132

[56] References Cited

U.S. PATENT DOCUMENTS

| | | | |
|---|---|---|---|
| 3,133,104 | 10/1984 | Sprauer | 585/540 |
| 3,399,245 | 8/1968 | Knapp | 585/540 |
| 3,453,084 | 7/1969 | Ivernel et al. | 585/540 |
| 3,541,179 | 11/1970 | Okagami et al. | 585/540 |
| 4,136,015 | 1/1979 | Kamm et al. | 208/129 |
| 4,199,533 | 4/1980 | Benson | 585/500 |
| 4,443,644 | 4/1984 | Jones et al. | 585/500 |
| 4,443,649 | 4/1984 | Jones et al. | 585/500 |
| 4,444,984 | 4/1984 | Jones et al. | 585/500 |

FOREIGN PATENT DOCUMENTS 908351 10/1962 United Kingdom ............... 208/106

*Primary Examiner*—Asok Pal
*Attorney, Agent, or Firm*—Alexander J. McKillop; Michael G. Gilman; Charles J. Speciale

[57] ABSTRACT

Methane is converted to higher, more reactive, hydrocarbon products by a diffusion flame. Methane is converted to $C_2+$ products by pyrolysis in the interior of the flame with oxidizing gas flowing outside of the flame. More reactive products are withdrawn from the center of the flame by a probe tube and cooled by the flowing oxidizing gas to stop the reaction.

10 Claims, 9 Drawing Figures

FLAME CONVERSION OF METHANE TO MORE REACTIVE HYDROCARBONS

BACKGROUND OF THE INVENTION

The present invention relates to the direct conversion of methane to $C_{2+}$ hydrocarbons and more particularly, to a diffusion flame technique for converting the hydrocarbons.

The conversion of hydrocarbon gases, particularly natural gas, to more reactive, higher hydrocarbon products is desirable because of the greater value of the products produced. The composition of natural gas at the wellhead varies but the major hydrocarbon present is methane. Large-scale use of natural gas often requires a sophisticated and extensive pipeline system. Liquefaction has also been employed as a transportation means, but processes for liquefying, transporting, and revaporizing natural gas are complex, energy-intensive, and require extensive safety precautions.

Indirect conversion of methane to enhanced value products has been practiced, such as catalytic steam reforming to produce gas for use in methanol synthesis or the Fischer-Tropsch process.

Among the different approaches that are known are the conversion of methane over a bed of various metal oxides as described by U.S. Pat. Nos. 4,443,644; 4,443,649; and 4,444,984, Jones et al. The Benson process, which utilizes a reaction between methane and chlorine to yield primarily ethylene and acetylene is described in U.S. Pat. No. 4,199,533.

The present invention is distinguished from these processes in that no catalyst bed is required, nor is a highly reactive corrosive gas required.

It is an object of the present invention to avoid catalyst aging problems and corrosive gas handling problems associated with methane conversion.

SUMMARY OF THE INVENTION

In accordance with the present invention, hydrocarbon gas is burned in a diffusion flame which converts the gas to more reactive products by pyrolysis in the center of the flame. The converted products are withdrawn from the center of the flame. Oxidizing gas flows outside of the flame. These higher, more reactive, products are withdrawn through this flowing oxidizing gas, thereby cooling the withdrawn products to stop the reaction. The residence time is controlled by controlling the position of withdrawal from the flame and/or by controlling the hydrocarbon gas flow rate.

The present invention provides advantages over prior art techniques of methane conversion, since it avoids catalyst aging problems and corrosive gas problems associated with prior art methods. Instead, the invention relies only on a diffusion flame to provide the required time/temperature conditions for converting methane to $C_{2+}$ products, which are withdrawn from the flame. The flame itself acts as a "pyrolysis reactor."

The foregoing and other objects, features and advantages of the invention will be better understood from the following more detailed description and appended claims.

SHORT DESCRIPTION OF THE DRAWINGS

DESCRIPTION OF THE PREFERRED EMBODIMENT

Figure 1:
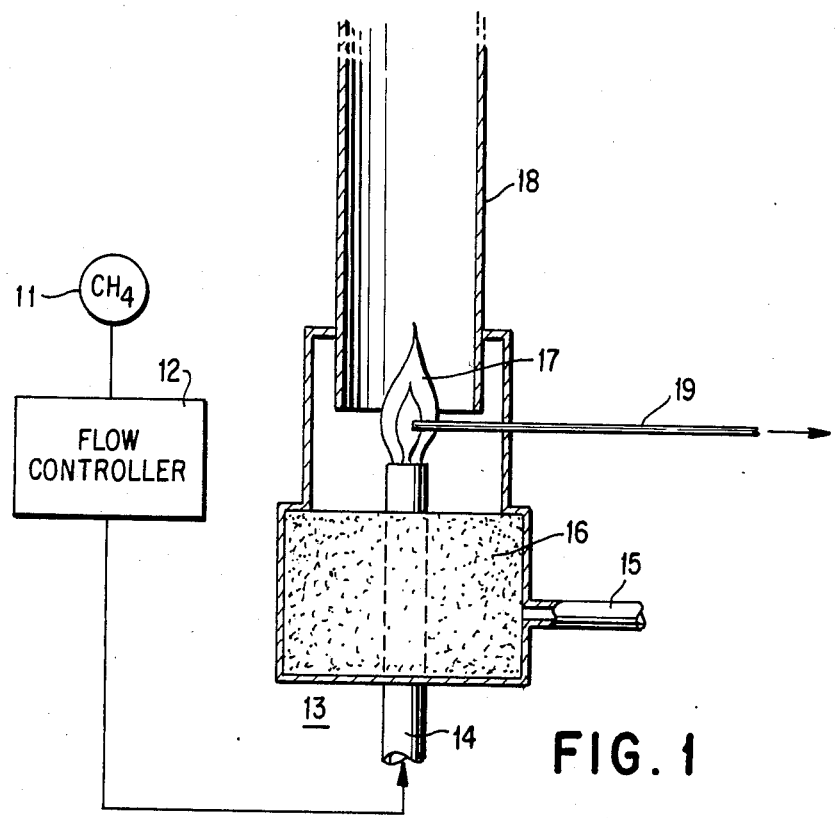
FIG. 1 depicts the diffusion flame apparatus of the present invention.

In FIG. 1, methane from a source 11 is fed through flow controller 12 to the diffusion flame burner 13 which includes burner tube 14, with the hydrocarbon gas being supplied to the bottom of the tube. Oxidizing gas flows past the top of burner tube 14. In an exemplary embodiment, a 40% $O_2$/60% $N_2$ mixture was fed to the inlet 15. The oxidizing gas flows through the coarse steel wool 16 upwardly past the top end of burner tube 14.

A diffusion flame 17 is produced at the top of burner tube 14. A chimney 18 carries away soot and other combustion product. More reactive products are withdrawn from the center of the flame by the probe tube 19. The products are cooled convectively by the flowing oxidizing gas stream around the flame. This rapidly quenches the more reactive products, thereby stopping the reaction as desired.

As used herein, "diffusion flame" is one wherein fuel without oxidizing gas mixed therein, is burned in a flame with oxidizing air being supplied to the outside of the flame. The reaction in the center of the flame is complex. Basically, it is pyrolysis wherein hydrogen atoms are stripped from the hydrocarbon gas. More reactive, higher carbon number products are produced. Initially, $CH_3$ is produced and the $CH_3$ radicals combine to produce $C_{2+}$ products. For example, acetylene, $C_2H_2$; ethylene, $C_2H_4$; and ethane, $C_2H_6$ are produced. Further dehydrogenation and radical chain growth also occurs, leading to production of more complex propylene and butadiene, depending on the residence time in the flame.

The present invention provides a simple way to convert methane to $C_{2+}$ materials which are valuable petrochemical feedstocks. The ultimate conversion levels of methane to $C_{2+}$ can be maximized simply by recycling to the flame any unreacted methane which is collected, making the process multi-pass.

While a single diffusion flame has been shown for converting dehydrocarbon gas, alternatively, a ring of flames with an oxygen deficient zone in the center thereof can be the diffusion flame. A burner for producing such a flame is shown in "FLAME REACTOR FOR CRACKING HYDROCARBONS", Green and Yan, filed 11/8/1986, U.S. Pat. Ser. No. 796,382.

Figure 2:
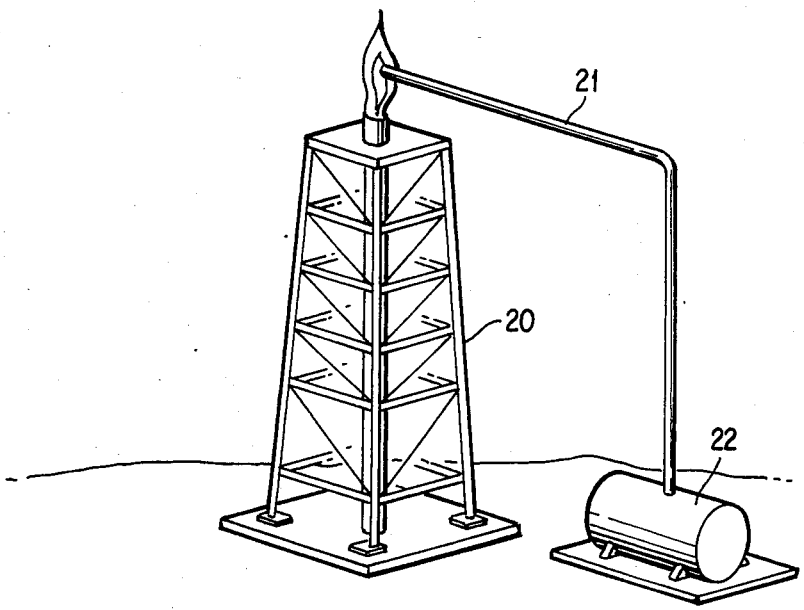
FIG. 2 depicts the invention practiced at a drilling site.

The practice of the invention is especially attractive in instances where methane has virtually no value. In particular, at drilling sites, methane is commonly flared as waste. FIG. 2 depicts the invention at the top of a tower 20 wherein methane is flared at the top. In accordance with the present invention, probe tube 21 is inserted into the flame to collect these valuable, more reactive, products in the collection tank 22.

EXAMPLES

The following examples were performed with the laminar diffusion flame burner shown in FIG. 1.

Methane was precisely metered to the burner via a mass flow controller at rates from 100 to 300 cc/min, while a 40% $O_2/N_2$ mixture was supplied separately to the burner at a flow of 12.5 l/min. Products were withdrawn from the flame using either a stainless steel or quartz capillary sampling probe, collecting at a rate of approximately 5 cc/min. The reaction products were rapidly quenched by the withdrawal through the sampling probe which is cooled convectively by the flowing $O_2/N_2$ gas stream around the flame.

Figure 3:
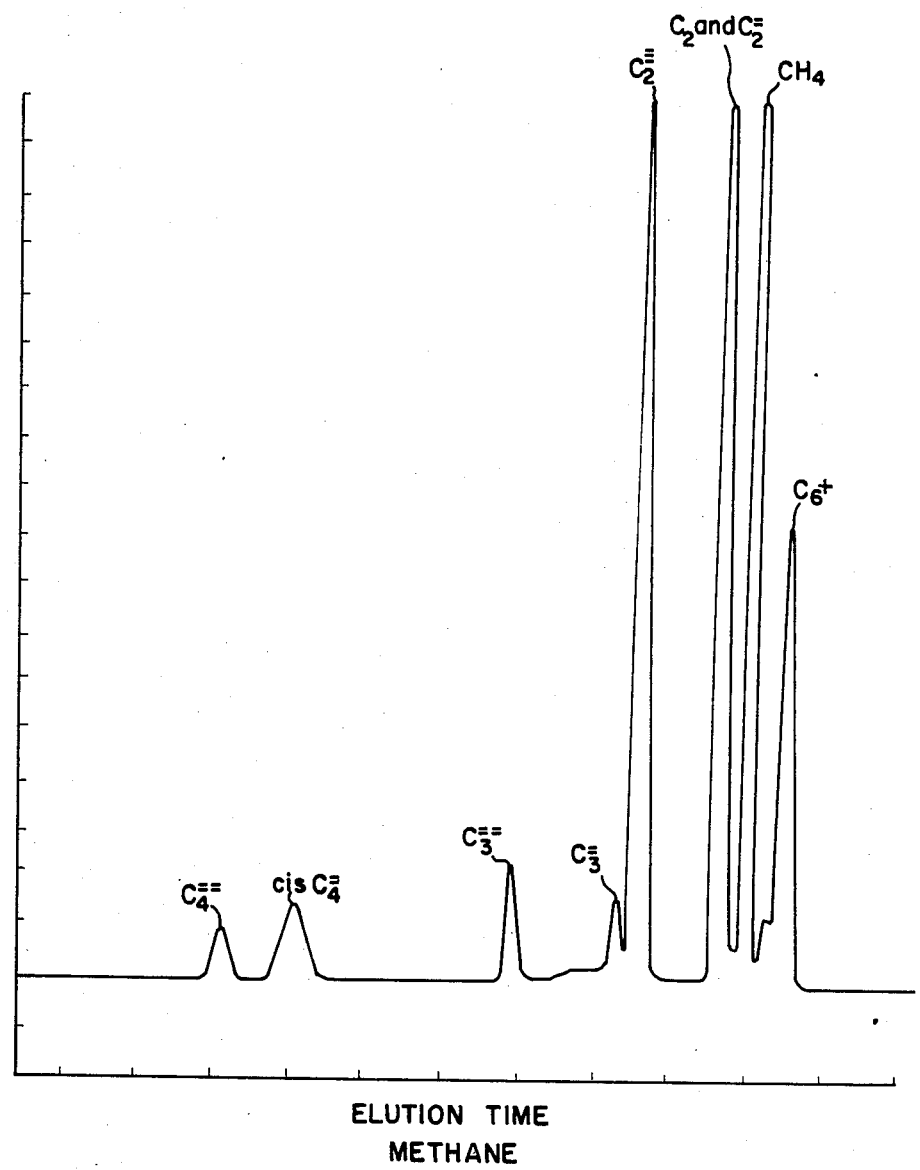
FIG. 3 shows a gas chromatogram of the hydrocarbon products withdrawn from a methane diffusion flame reaction.

FIG. 3 shows a gas chromatogram of the gases sampled from a methane diffusion flame burning as described above. These gases were collected at a point corresponding to a residence time of approximately 200 msec. An analysis of the hydrocarbons shows the presence of ethane, ethylene, acetylene, propylene, propadiene, butene, butadiene, as well as some $C_5$ material and unreacted methane. This particular run 5 resulted in a $C_2$ selectivity of 86% and a methane conversion level to $C_2$ of 2.2%, on a hydrocarbon basis alone; ethylene and acetylene comprised the bulk of the $C_2$ mixture. Free hydrogen, nitrogen, CO, $CO_2$, and small quantities of oxygen were also detected in the sampled gas stream.

Figure 4:
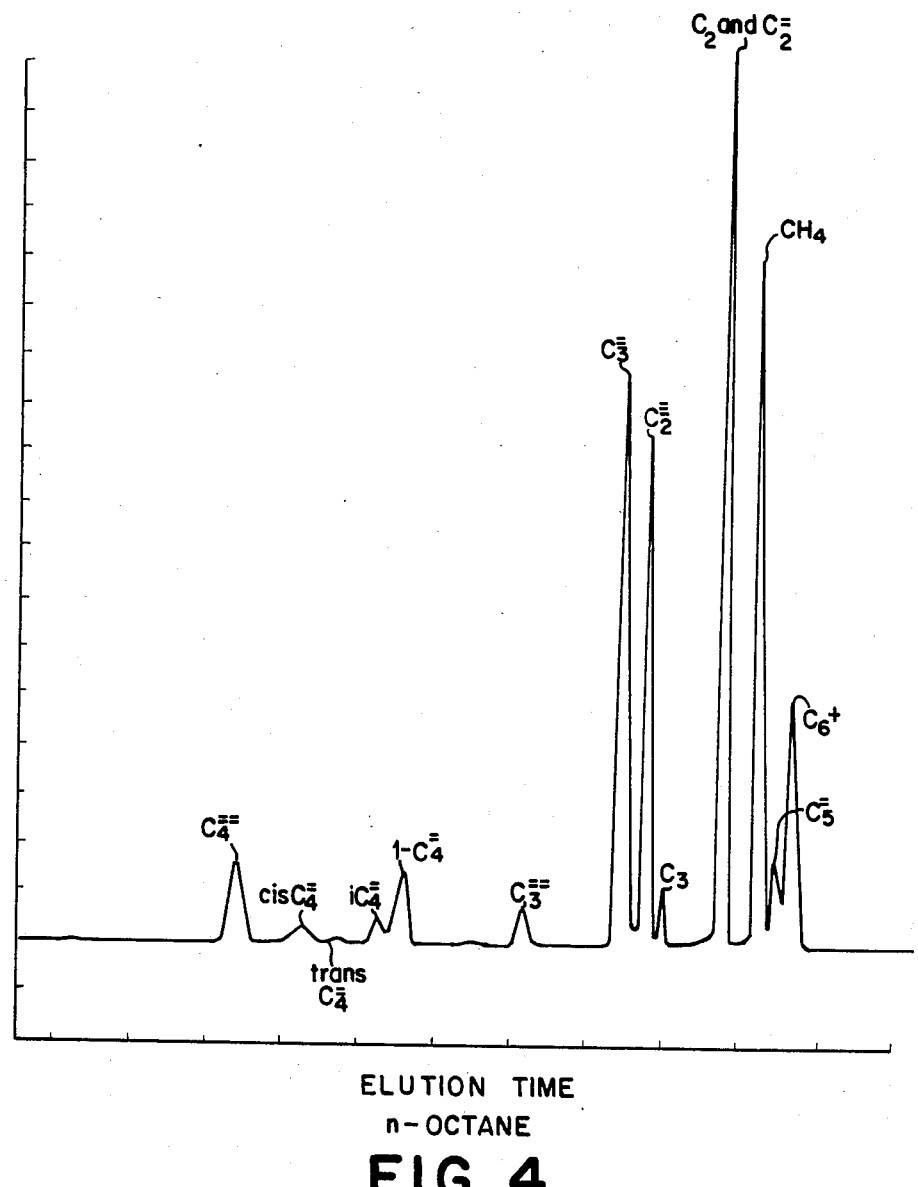
FIG. 4 shows a gas chromatogram of the hydrocarbon products withdrawn from an n-octane flame reaction.
Figure 5:
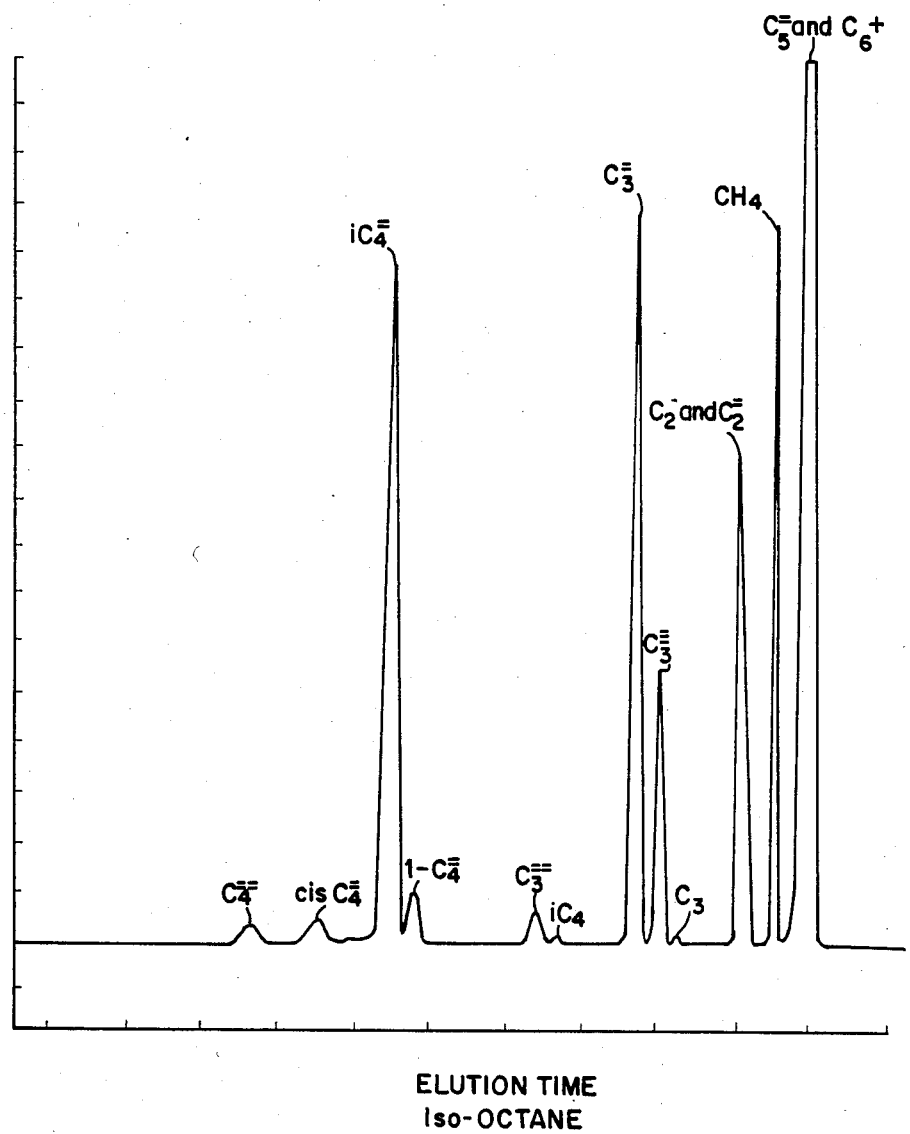
FIG. 5 shows a gas chromatogram of the hydrocarbon products withdrawn from an iso-octane flame reaction.
Figure 6:
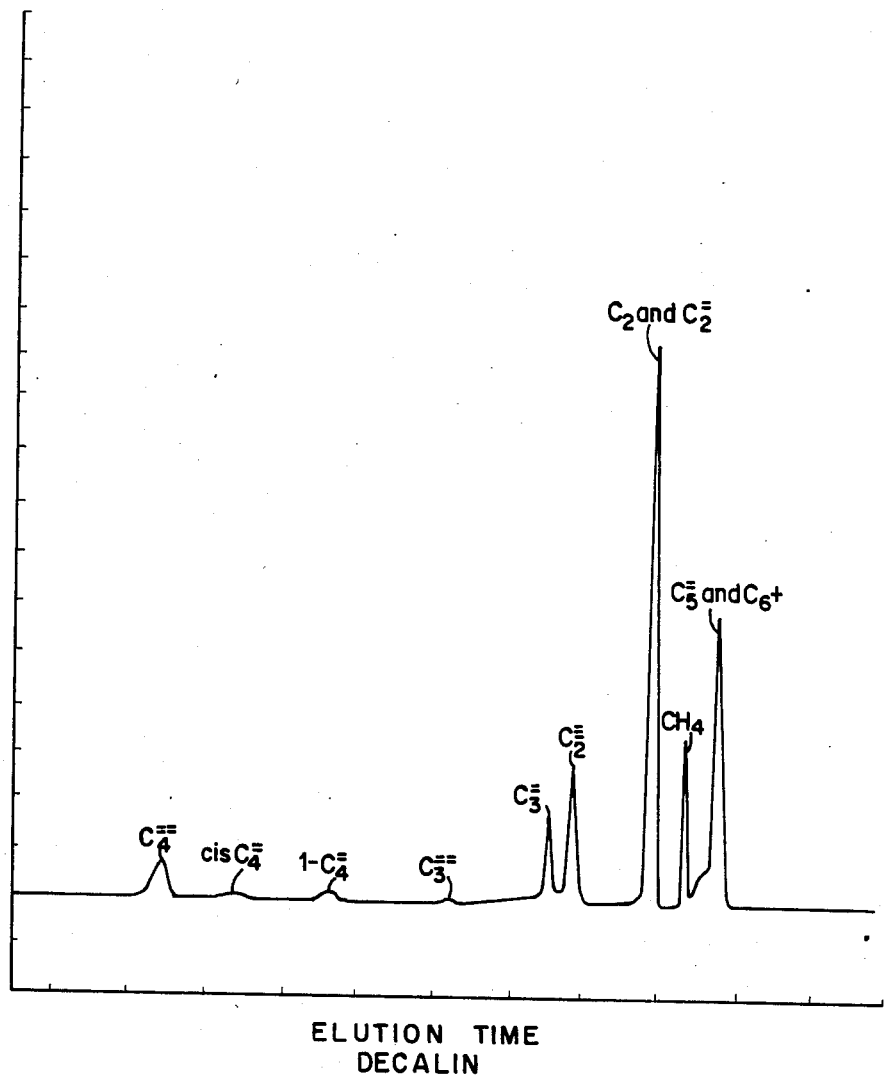
FIG. 6 shows a gas chromatogram of the hydrocarbon products withdrawn from a decalin flame reaction.

FIGS. 4, 5 and 6 show gas chromatograms of sampled product gases from n-octane, iso-octane, and decalin diffusion flames, demonstrating the applicability of the concept to higher carbon number, saturated materials. Among the major products are unsaturates such as ethylene, acetylene, propylene, butylene and butadiene.

By controlling the residence time in the flame, the type of reaction product produced can be controlled. This is demonstrated by FIGS. 7-9, which show gas chromatograms of sample product gases when methane was burned, but the gas was withdrawn from different positions in the flame.

In each case, the methane flow rate is twice that of the example corresponding to FIG. 3.

Figure 7:
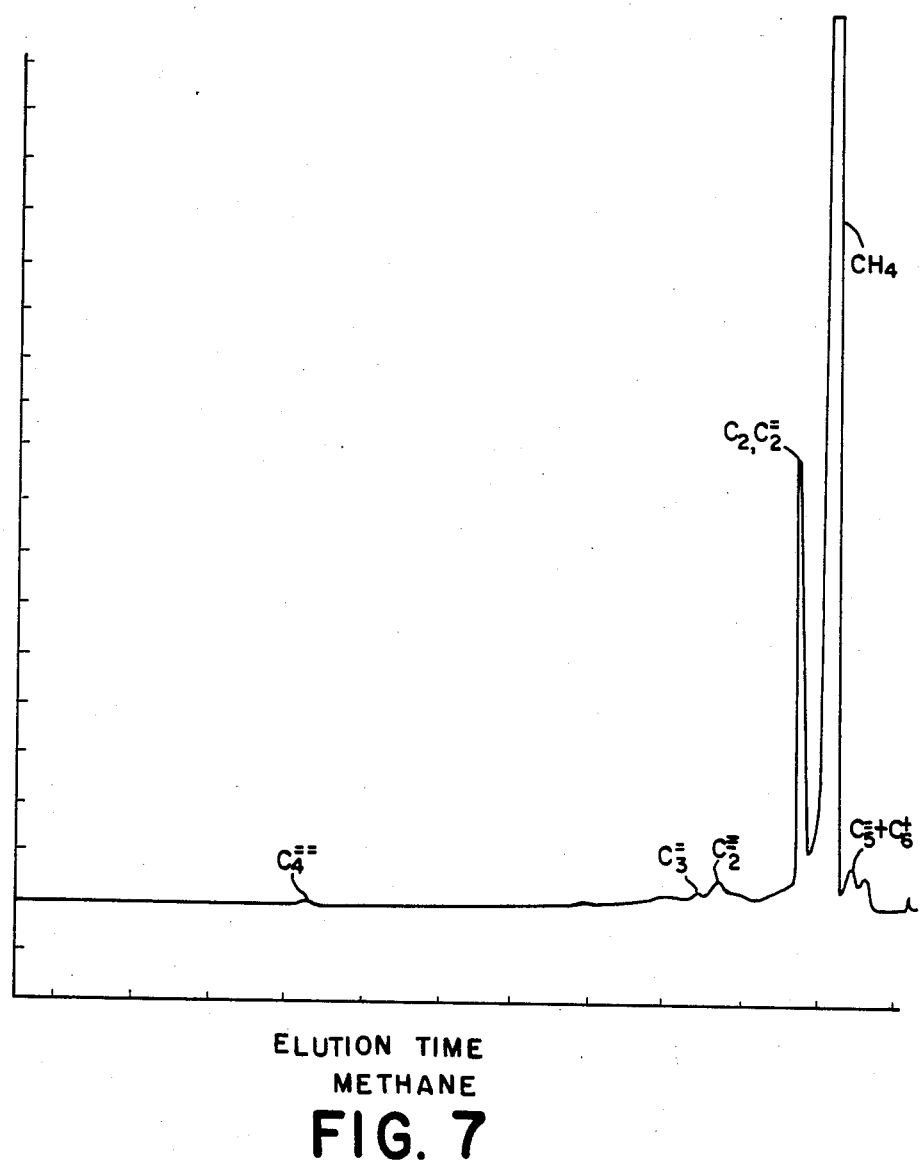
FIGS. 7-9 are gas chromatograms of the hydrocarbon products withdrawn from a methane diffusion flame reaction, from different positions in the flame.

FIG. 7 was produced when products from a methane diffusion flame were sampled at a position corresponding to a point approximately 25% up the centerline of the flame, measured from the gas inlet. The flow rate is 300 cc/min.

Figure 8:
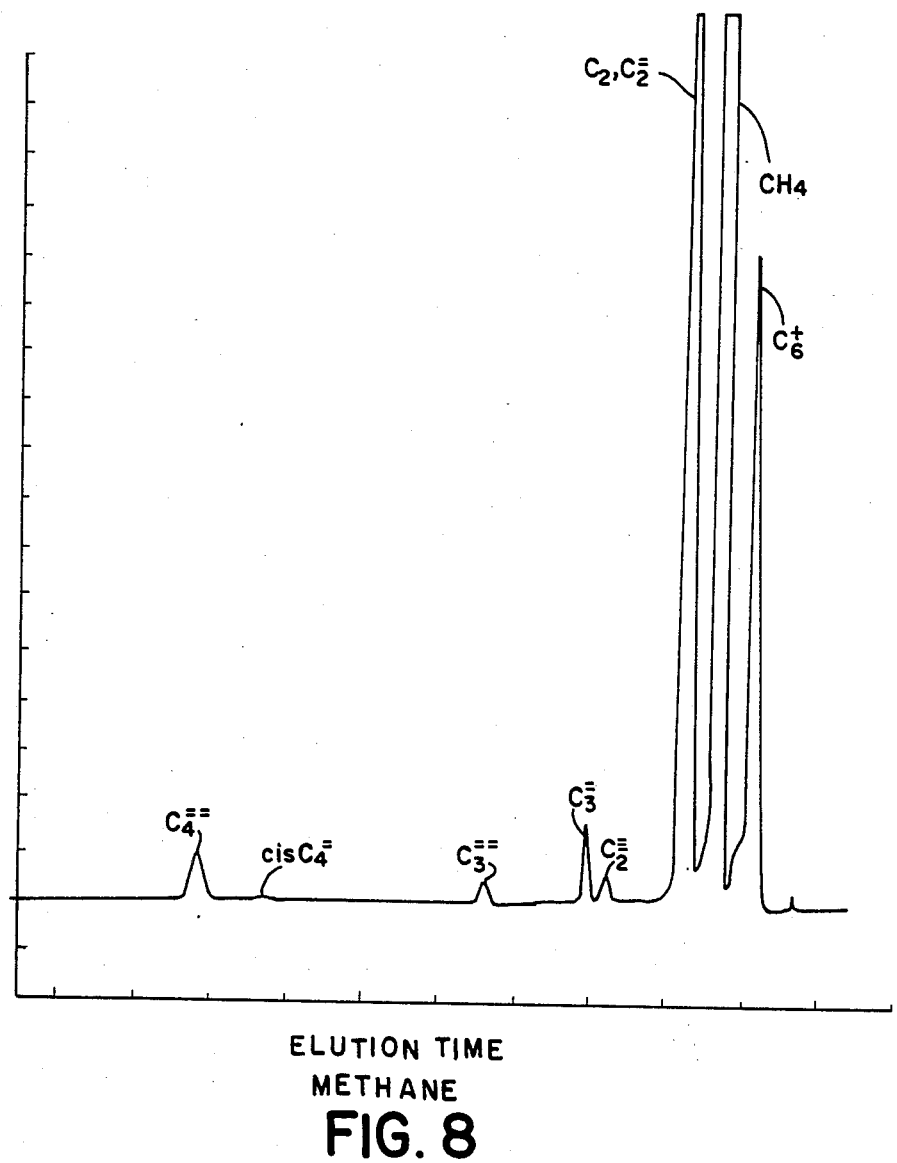

FIG. 8 is the same as FIG. 7 above, except the sampling point is approximately 50% up the centerline of the flame.

Figure 9:
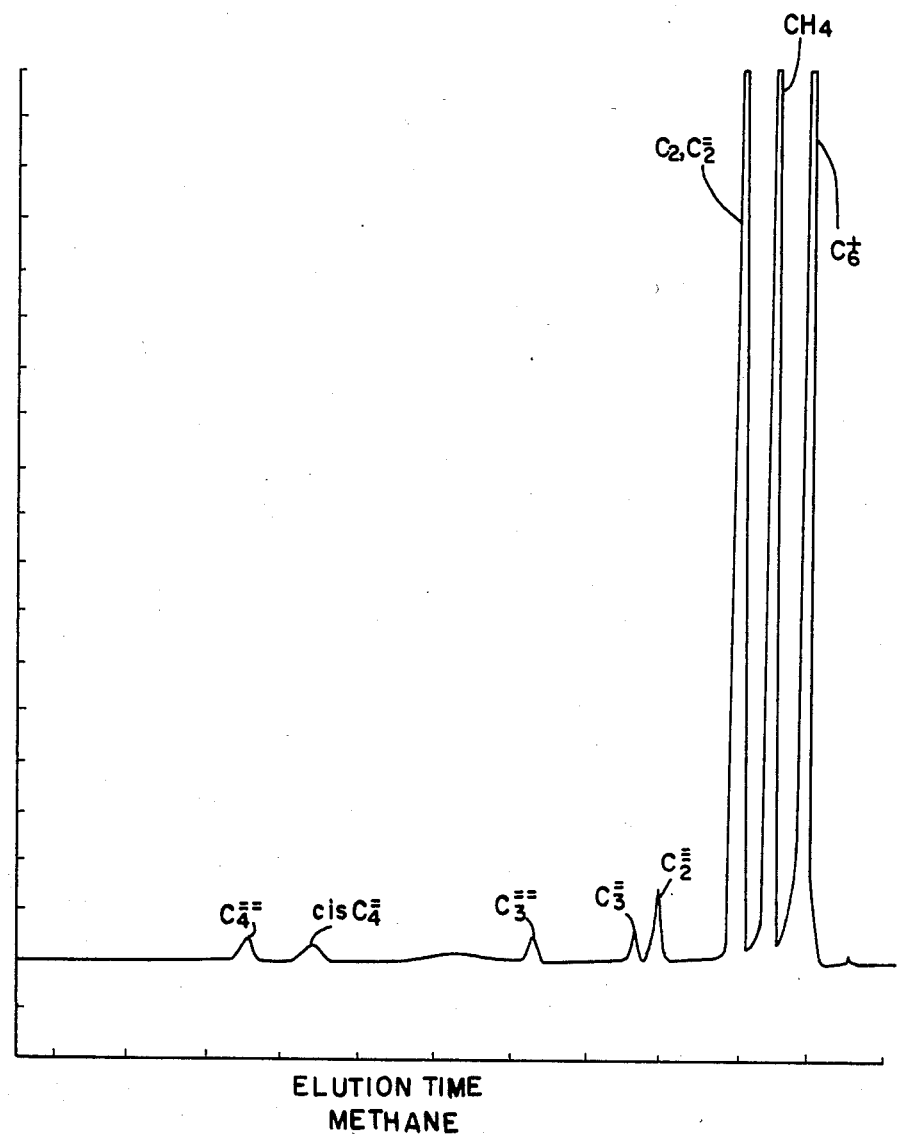

FIG. 9 is the same as FIG. 8 above, except the sampling point is approximately 75% up the centerline of the flame.

When compared to the example of FIG. 3, these examples clearly demonstrate the variety of product distributions that can be obtained by varying the sampling position in the flame as well as the flow rate of the feed methane.

FIGS. 3-9 were produced by a Carle refinery gas analyzer.

While a particular embodiment of the invention has been shown and described, various modifications are within the true spirit and scope of the invention. The appended claims are, therefore, intended to cover all such modifications.

What is claimed is:

1. The method of coverting hydrocarbon gas to $C_2+$ products comprising:
   supplying the hydrocarbon gas to be converted to the oxygen-deficient interior of a diffusion flame;
   heating the hydrocarbon gas in the oxygen-deficient interior of said diffusion flame;
   converting said hydrocarbon gas to said $C_2+$ products by pydrolysis in the oxygen-deficient interior of said diffusion flame; and
   withdrawing the converted products from the oxygen-deficient interior of said diffusion flame without mixing with the combustion products.

2. The method recited in claim 1 further comprising: flowing oxidizing gas outside of said diffusion flame.

3. The method recited in claim 1 further comprising: burning said hydrocarbon gas at atmospheric pressure.

4. The method recited in claim 1 further comprising: cooling the withdrawn products to stop the reaction after withdrawal.

5. The method recited in claim 4 wherein the step of cooling is carried out by passing the withdrawn gas through the flowing oxidizing gas.

6. The method recited in claim 1 wherein methane gas is converted to $C_2+$ products.

7. The method recited in claim 6 wherein said $C_2+$ products are from the group consisting of acetylene, ethylene, ethane, propylene, butylene and butadiene.

8. The method recited in claim 1 further comprising: controlling the residence time of said gas in the interior of said flame to control the type of reactive products which are produced.

9. The method recited in claim 1 wherein said oxidizing gas is a mixture of oxygen and nitrogen.

10. The method recited in claim 1 wherein said hydrocarbons to be converted are from the group consisting of methane, n-octane, iso-octane and decalin.

* * * * *